(12) United States Patent
Dreyfuss et al.

(10) Patent No.: US 8,579,940 B2
(45) Date of Patent: Nov. 12, 2013

(54) SUTURE ANCHOR WITH APERTURES AT TIP

(75) Inventors: Peter J. Dreyfuss, Naples, FL (US); William C. Benavits, Naples, FL (US)

(73) Assignee: Arthrex, Inc., Naples, FL (US)

( * ) Notice: Subject to any disclaimer, the term of this patent is extended or adjusted under 35 U.S.C. 154(b) by 2007 days.

(21) Appl. No.: 11/097,180

(22) Filed: Apr. 4, 2005

(65) Prior Publication Data

US 2005/0222619 A1 Oct. 6, 2005

Related U.S. Application Data

(60) Provisional application No. 60/559,426, filed on Apr. 6, 2004.

(51) Int. Cl.
*A61B 17/04* (2006.01)
(52) U.S. Cl.
USPC .......................................................... 606/232
(58) Field of Classification Search
USPC ............. 606/232, 72–74, 300, 301, 304, 323; 24/58, 90.1, 115, 114.7, 122.6, 130, 24/331; 411/395, 493–497, 499

See application file for complete search history.

(56) References Cited

U.S. PATENT DOCUMENTS

| | | | | |
|---|---|---|---|---|
| 1,610,309 | A | * | 12/1926 | Niederer ..................... 24/114.1 |
| 5,156,616 | A | | 10/1992 | Meadows et al. |
| 5,306,290 | A | | 4/1994 | Martins et al. |
| 5,370,662 | A | | 12/1994 | Stone et al. |
| 5,480,403 | A | * | 1/1996 | Lee et al. ..................... 606/232 |
| 5,571,139 | A | | 11/1996 | Jenkins, Jr. |
| 5,885,294 | A | | 3/1999 | Pedlick et al. |
| 6,436,124 | B1 | * | 8/2002 | Anderson et al. ............. 606/232 |
| 2003/0065361 | A1 | * | 4/2003 | Dreyfuss ..................... 606/232 |

* cited by examiner

*Primary Examiner* — Dianne Dornbusch
(74) *Attorney, Agent, or Firm* — Dickstein Shapiro LLP

(57) ABSTRACT

A suture anchor includes a threaded anchor body having a bore for receiving a driver, and at least two distal passageways extending from the bore to corresponding apertures at the distal end of the suture anchor. The apertures are provided as pairs with a corresponding groove formed between the apertures of the pair. Suture strands can be inserted into the suture anchor through the apertures, the distal portion of the sutures seated in the grooves between the apertures being protected from abrasion during installation of the suture anchor.

9 Claims, 4 Drawing Sheets

SUTURE ANCHOR WITH APERTURES AT TIP

This application claims the benefit of U.S. Provisional Application Ser. No. 60/559,426, filed Apr. 6, 2004.

BACKGROUND OF THE INVENTION

1. Field of the Invention

The present invention relates to an apparatus for anchoring surgical suture to bone. More specifically, the present invention relates to a suture anchor having apertures at the distal tip thereof for anchoring sutures in the cortical bone during arthroscopic surgery.

2. Description of the Related Art

When soft tissue tears away from bone, re-attachment becomes necessary. Various devices, including sutures, screws, staples, wedges, and plugs have been used in the prior art to secure soft tissue to bone.

Recently, various types of threaded suture anchors have been developed for this purpose. Some threaded suture anchors are designed to be inserted into a pre-drilled hole. Other suture anchors are self-tapping.

U.S. Pat. No. 5,156,616, for example, discloses a suture anchor which has an axial passageway extending through the suture anchor. The passageway has a proximal portion, a central portion, and a distal portion. The proximal portion is hexagonally-shaped to cooperate with a hex driver for installing the anchor. The distal portion is sized to receive a knotted piece of suture, and the central portion has a diameter less than the that of the proximal and distal portions to receive the suture being threaded therethrough. Use of the suture anchor disclosed in the '616 patent, however, requires tying a suture knot. If the knot is not tied securely or if the knot is not made large enough, there is a risk that the knot will unravel or be pulled through the distal portion of the passageway.

Another prior art suture anchor is disclosed in U.S. Pat. No. 5,370,662 and has an eyelet located on the proximal end of the anchor through which a suture can be passed. Since the eyelet is formed as part of the drive head, however, combining these two functions in one structure often tends to weaken the drive head.

Problems can arise if the structure for attaching the suture fails, allowing the suture to become detached from the anchor. For example, if the suture anchor is biodegradable, the eyelet can degrade rapidly, causing the suture to become detached from the anchor prematurely.

Further, such a prior art suture anchor having an eyelet extending from the proximal end thereof requires countersinking of the eyelet below the bone surface to avoid having the patient's tissue abrade against the exposed eyelet. As a result, suture attached to the eyelet is vulnerable to abrasion by the bony rim of the countersunk hole into which the suture anchor is installed.

In addition, various other modifications to the drive head often are employed in connection with suture attachment. For example, recessed grooves may be formed on opposite sides of the drive head to receive and protect the suture from abrasive areas of the suture anchor tunnel or to facilitate mating between the anchor to the driver. In such cases, the drive head often must be made of a larger diameter to recover the mechanical strength lost from the removal of material relating to the suture-attachment or suture-protection modifications.

Accordingly, a need exists for a threaded suture anchor to which suture is secured effectively so as to prevent detachment of the suture. In addition, a need exists for suture anchors that will not abrade tissue and do not require countersinking.

SUMMARY OF THE INVENTION

The present invention provides a suture anchor which securely affixes sutures to the anchor without subjecting the sutures to abrasion by the surrounding bone or subjecting the tissue to be secured with the suture anchor to be abraded by the sutures. Moreover, the suture anchor according to the present invention can be installed without countersinking.

The suture anchor according to the present invention includes a threaded anchor body having a bore for receiving a driver, and preferably four distal passageways extending from the bore to four corresponding apertures at the distal end of the suture anchor. In this embodiment, the apertures are provided as two pairs with a corresponding groove formed between the apertures of each pair.

Suture strands can be inserted into the suture anchor through the apertures, and when the ends of the sutures are pulled as far as possible out the proximal end of the suture anchor, the portion of the sutures seated in the grooves are thereby protected from abrasion during installation of the suture anchor.

Other features and advantages of the present invention will become apparent from the following description of the invention, which refers to the accompanying drawings.

DETAILED DESCRIPTION OF THE PREFERRED EMBODIMENT

In the following detailed description, reference is made to various specific embodiments in which the invention may be practiced. These embodiments are described with sufficient detail to enable those skilled in the art to practice the invention, and it is to be understood that other embodiments may be employed, and that structural and logical changes may be made without departing from the spirit or scope of the present invention.

Figure 1:
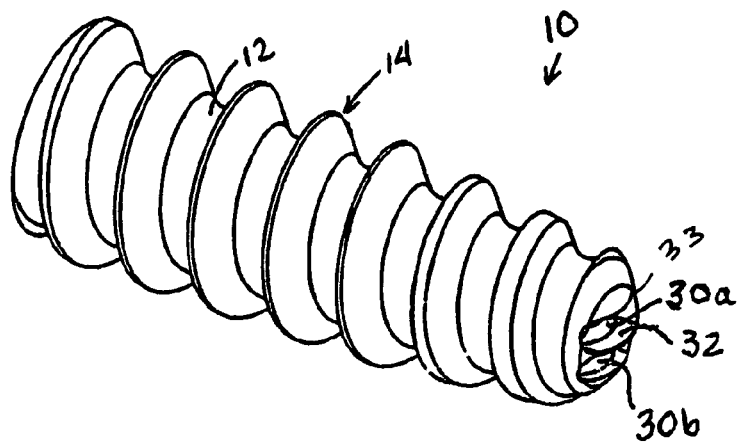
FIG. 1 is a perspective view of the suture anchor in accordance with the present invention.
Figure 2:
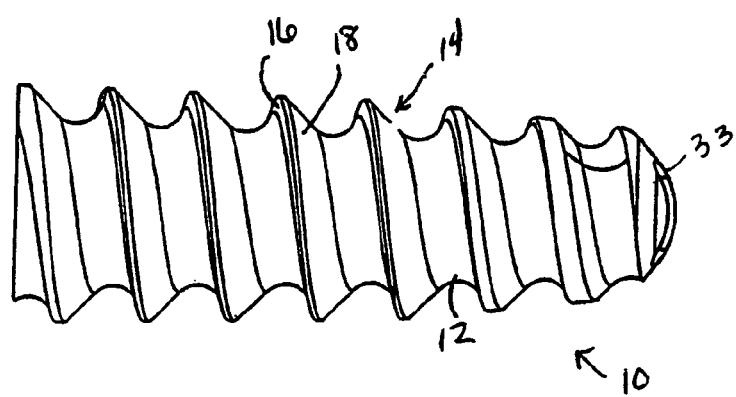
FIG. 2 is a side elevational view of the suture anchor shown in FIG. 1.
Figure 3:
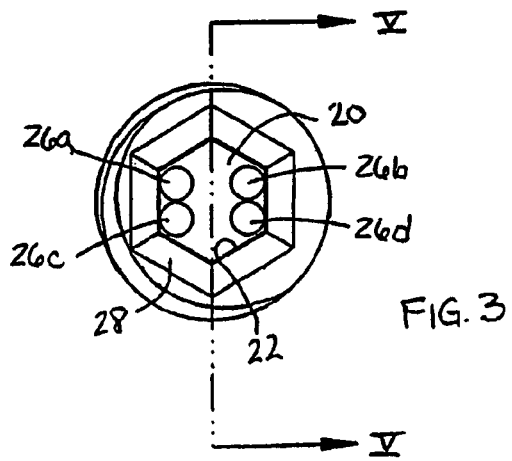
FIG. 3 is a view of the proximal end of the suture anchor of the present invention.
Figure 4:
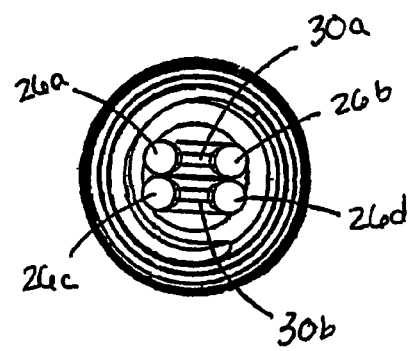
FIG. 4 is a view of the distal end of the suture anchor of the present invention.
Figure 5:
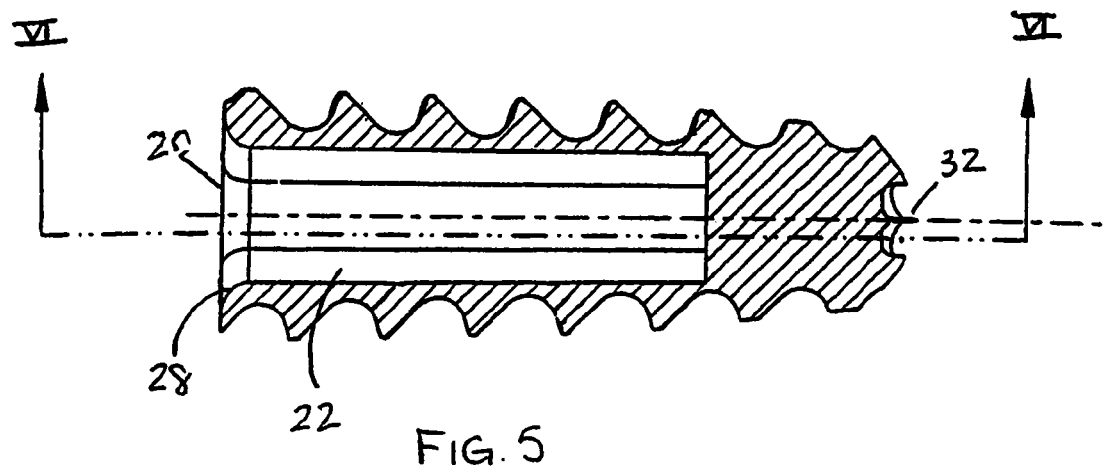
FIG. 5 is a cross-sectional view of the suture anchor through the plane V-V in FIG. 3.

Referring first to FIGS. 1 and 2, an exemplary embodiment of the suture anchor according to the present invention is identified generally by reference numeral 10. Suture anchor 10 includes a body 12 formed generally in the shape of a slightly tapered cylinder and having a blunt or slightly rounded distal end. In an exemplary embodiment, suture anchor 10 is provided with about eight flights of thread 14 wrapping around body 12, with the angle of the proximal surface 16 of each thread being approximately between one-third and one-fourth the angle of the distal surface 18 of each thread relative to the horizontal. For example, in the preferred embodiment, the proximal surface of each thread has an angle of 12° relative to a plane horizontal to the axis of the suture anchor, while the distal surface of each thread has an angle of 45° relative to the same horizontal plane.

In an exemplary embodiment, body 12 of suture anchor 10 has a length of about 0.6 in. and an exterior diameter of about 0.22 in. (5.5 mm) as measured across the outer diameter of the threading at the proximal end of the anchor.

Figure 6:
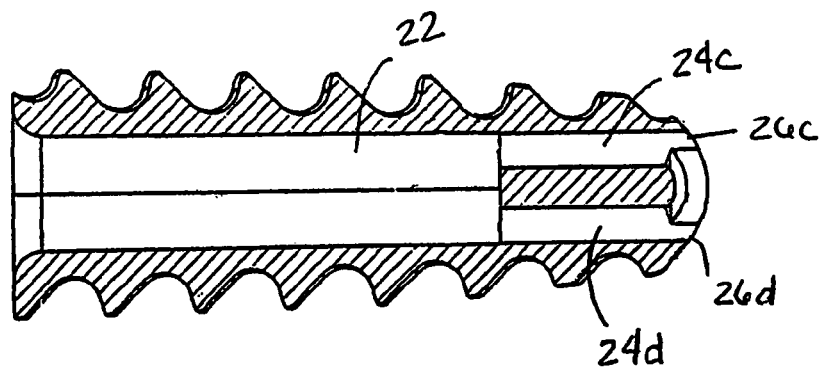
FIG. 6 is a cross-sectional view of the suture anchor through the plane VI-VI in FIG. 5.

Referring now to FIGS. 3-6, suture anchor 10 is provided with a bore 22 starting from an opening 20 at the proximal end and extending into the anchor body 12 approximately two-thirds of the length therethrough. Although FIGS. 3-6 illustrate bore 22 having a hexagonal cross-section, and although references to the bore 22 will be made in this application as to the hexagonal bore 22, the invention is not limited to this embodiment and contemplates suture anchors provided with central bores having various cross-sectional configurations. Distally of hexagonal bore 22, anchor body 12 is solid except for four passageways (only 24c and 24d are seen in FIG. 6) extending to four corresponding apertures 26a-26d on the curved surface of the distal end of suture anchor 10.

The four apertures 26a-26d are arranged in two pairs, i.e. 26a-26b and 26c-26d, with each pair defining the ends of a respective groove 30a, 30b formed at the distal end of suture anchor 10. The two grooves 30a, 30b are parallel and recessed from a most distal surface 33 of suture anchor 10 so as to define a ridge 32 between them.

Two strands of suture can be threaded into suture anchor 10, with the two ends of one suture strand being threaded through apertures 26a and 26b formed in groove 30a, and the two ends of another suture strand being threaded through apertures 26c and 26d in groove 30b. The ends of the suture strands are passed through the respective passageways 24a-24d and the hexagonal bore 22 to exit the suture anchor 10 from the proximal opening 20.

With sutures threaded through suture anchor 10 as described above, the view from the distal end of suture anchor 10 is similar to that of a button sewed onto an article of clothing with thread. When the sutures ends are pulled as far as possible out the proximal end of suture anchor 10, the portions of the sutures contacting the distal end surface of suture anchor lie in the grooves 30a, 30b between ridge 34 and the exterior walls of the grooves, and are protected from abrasion thereby.

The apertures 26a and 26c, and also 26b and 26d can be placed close together since they are not in the same groove; hence, there will be no force exerted on suture anchor body 12 between these respective apertures. On the other hand, the greater distance between apertures 26a and 26b, and also 26c and 26d at the ends of groove 30a and 30b, respectively, and the solid material of body 12 forming the regions between these pairs of apertures provide the structural integrity to support the stress exerted on the suture anchor 10 by the sutures threaded therethrough. In the preferred embodiment, the centers of the pair of apertures 26a, 26b and 26c, 26d formed in each groove 30a, 30b are spaced approximately 0.05 to about 0.08 in., more preferably approximately 0.065 in., apart, while the centers of adjacent apertures 26a, 26c and 26b, 26d from the opposing grooves are spaced much closer, e.g. approximately 0.032 in.

The proximal surface and associated edges of suture anchor 10 defining the hexagonally shaped opening 20 is rounded and smooth. Preferably, the proximal surface of the suture anchor 10 forming the periphery of the opening 20 forms a rounded lip 28 so that opening 20 has a slightly wider diameter than the main portion of hexagonal bore 22. Prior art anchors have sharp edges surrounding the drive opening, which are problematic in that any sutures passed through the central cannula of the anchor can be abraded by the sharp edges, thereby compromising the strength of the sutures. With the smooth and rounded proximal end provided in the anchor according to the present invention, sutures threaded through the apertures 26 will not become frayed upon pressure or rubbing against the anchor at the proximal opening.

As an alternative embodiment of the present invention, suture anchor body 12 can be provided with only two apertures 26 and one groove 30, or can be provided with more than two pairs of apertures and a corresponding number of grooves.

Preferably, suture anchor 10 is made from a bioabsorbable polymer material such as a polyglycolic or polylactic acid polymer, poly(1-lactide-co-d, 1-lactide) 70:30 (PLDLA) being most preferred. Also, it is preferred that the sutures used in connection with the inventive suture anchor are also bioabsorbable, such as No. 2 or No. 5 USP braided polyester.

Although PLDLA is the most preferred material for the suture anchor of the present invention, the suture anchor can be made from other bioabsorbable materials known in the art. As used herein, the term "bioabsorbable" is considered to be interchangeable with the term "biodegradable," "resorbable," and "absorbable" to mean that the device can be absorbed by the body over time. Also, the measurements, angles and ratios between the dimensions of the suture anchor may be varied from those described above so as to be suitable for the conditions and applications in which the suture anchor is to be used.

Optionally, the suture anchor can be distributed with at least one strand of suture already threaded through the apertures 26a-26d.

Figure 7:
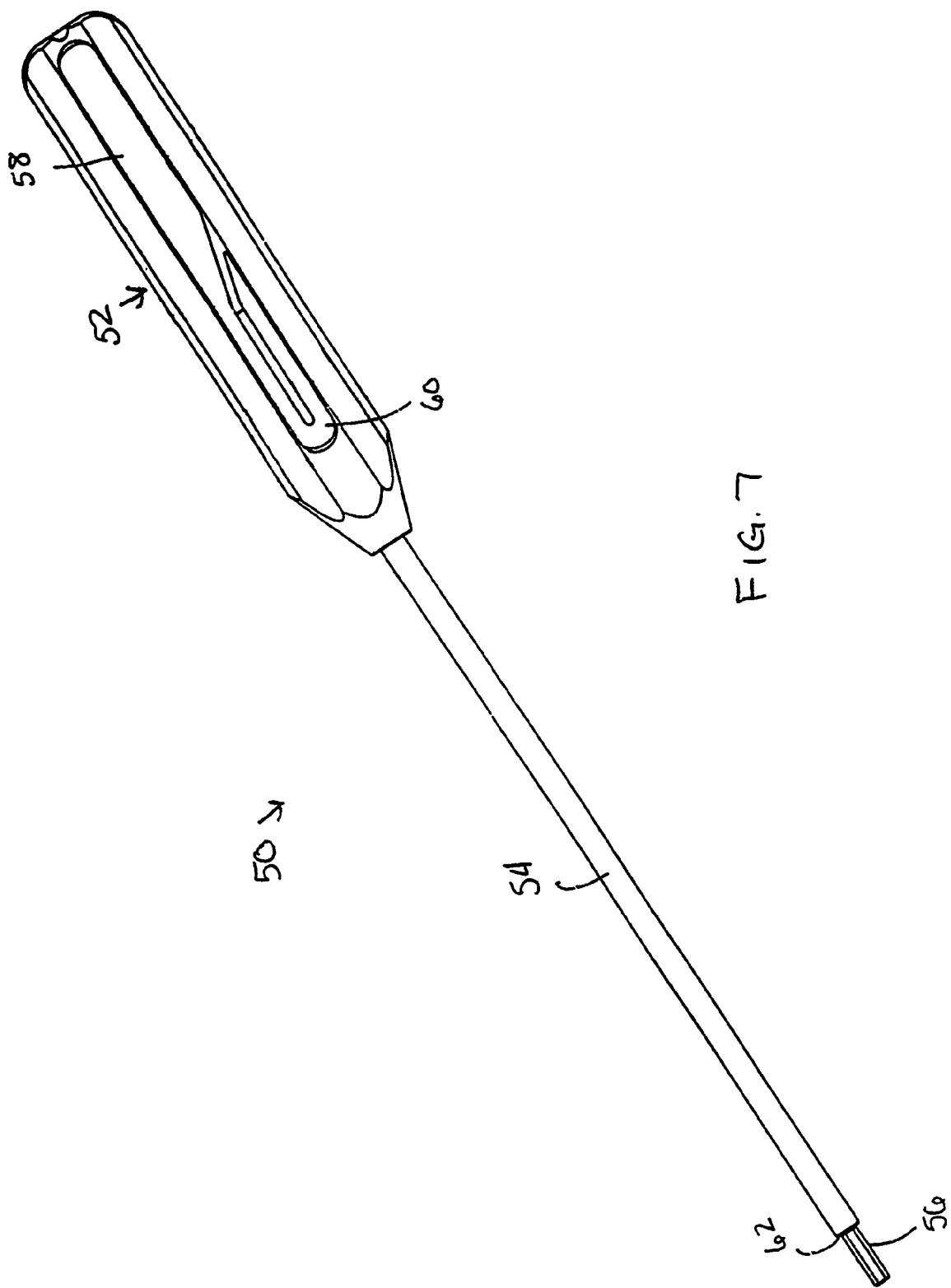
FIGS. 7 and 8 are side elevational views of a driver used in connection with the suture anchor of the present invention.
Figure 8:
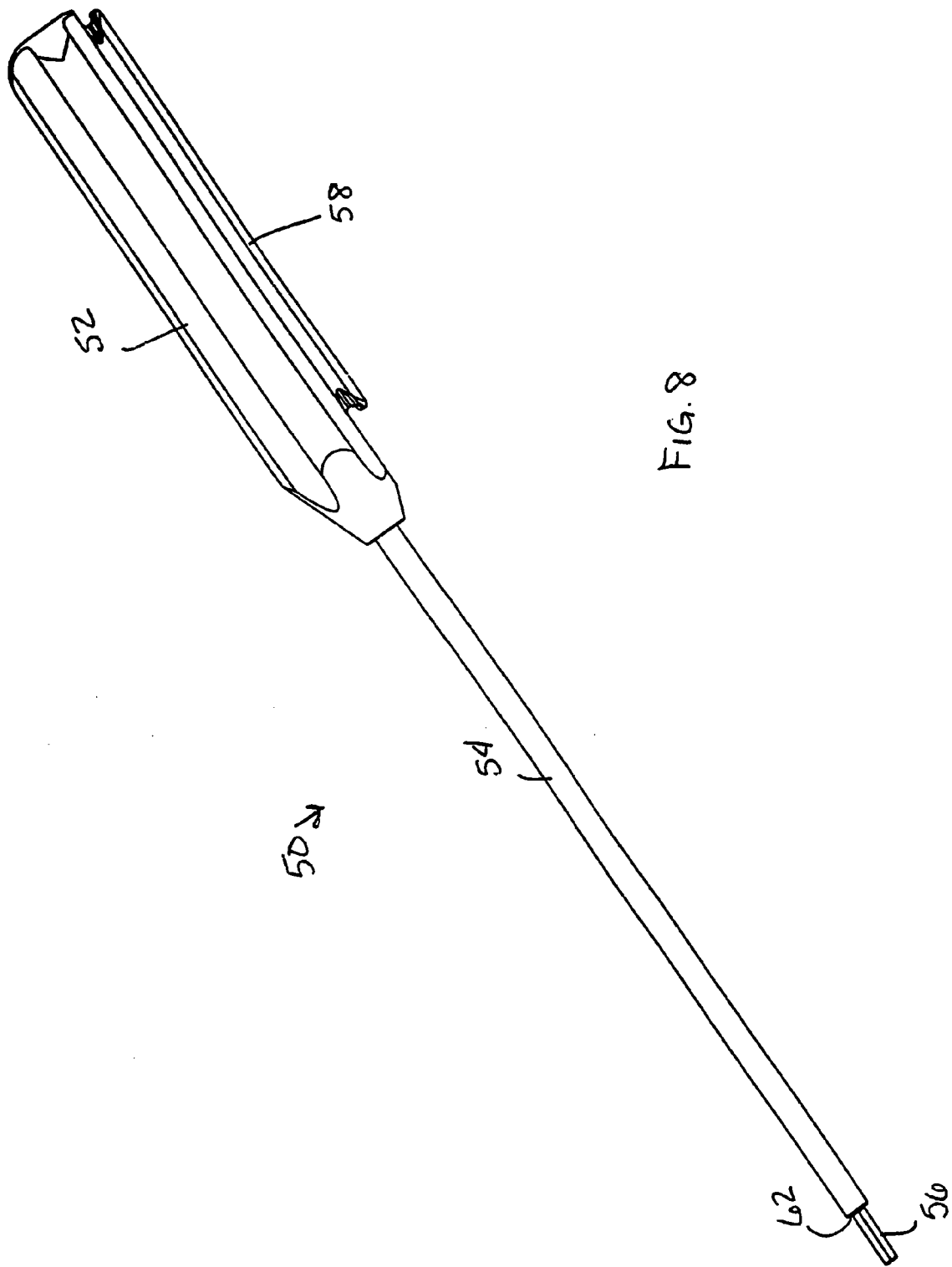

A driver such as that shown in FIGS. 7 and 8 is used to install the suture anchor 10 of the present invention during an arthroscopic procedure. Driver 50 has a handle 52, a shaft 54, and a drive head 56. Drive head 56 is hexagonally shaped and has a width and a length which substantially corresponds to the width and length of hexagonal bore 22 in suture anchor 10. Preferably, the drive head is slightly shorter and has a slightly smaller width than bore 22, so that the fit is not too tight, yet ensures secure engagement for driving the suture anchor into bone.

Driver 50 is cannulated throughout the length thereof, with a distal opening at the distal face of drive head 56 and a proximal opening at the proximal surface of handle 52. Sutures threaded through suture anchor 10 from apertures 26a-26d at the distal end thereof and exiting through the proximal opening 20 can thus be passed through the cannula through driver 50 when drive head 56 is to be engaged with bore 22 in suture anchor 10 for driving the same.

Handle 52 preferably includes an elongated double hook 52 extending substantially along the length thereof and having a hook at the proximal end and at the distal end thereof, and a clip 60 formed at one end region of the double hook 52. When driver 50 is engaged with suture anchor 10, excess lengths of suture passed through the proximal end of driver 50 can be wrapped around the double hook 52, and the ends of the sutures can be secured in the clip 60. In this manner, the suture strands can be prevented from becoming tangled or otherwise interfering with the surgeon's work.

Driver 50 is preferably constructed to withstand an application of 20 in/lb of torque. Preferably, though not necessarily, at least the shaft 54 and drive head 56 are made of stainless steel. However, other materials may be used which provide the necessary strength and rigidity for installing the suture anchor of the present invention into cortical bone.

To install the suture anchor of the present invention, a hole is pre-formed in the bone, either with a punch or a drill. Preferably, the diameter of the hole formed is slightly (e.g. 1 mm) smaller than the diameter of the suture anchor to be installed, to ensure good purchase of the suture anchor threads in the bone.

The ends of the suture strands threaded through the suture anchor 10 are then threaded through the cannula in driver 50, and the distal end of the hexagonal drive head 56 of the driver is then inserted into the hexagonal bore 22 of the anchor 10 so that the shoulder 62 forming the transition between the drive head 56 and the drive shaft 54 abuts the lip 28 at the proximal surface of suture anchor 10. If necessary or applicable, excess lengths of the sutures exiting the proximal end of driver 50 are wrapped around the double hook 58 and/or clipped in clip 60.

The suture anchor is then placed at the opening of the prepared hole in the bone, and the driver 50 is rotated until the proximal surface of the anchor is flush with the surface of the bone. Since it is not necessary for the proximal end of the anchor to be countersunk below the bone surface to prevent tissue abrasion, as is required with prior art devices, the inventive anchor does not need to be inserted as far as prior art devices, and avoids abrasion of the sutures by the rim of the bone around the installed suture anchor.

The suture anchor of the present invention provides advantages in addition to those already discussed above. For example, with the threads provided along the entire length of the suture anchor body, the anchor is afforded maximum securement by the threads in the cortical bone, unlike some prior art anchors in which the threads only contact the cancellous bone. Also, the significant depth of the hexagonal bore for receiving the driver allows the suture anchor to be installed with a higher torque than many prior art anchors, thus imparting greater fixation strength to the installed anchor of the present invention.

Although the present invention has been described in relation to particular embodiments thereof, many other variations and modifications and other uses will become apparent to those skilled in the art. Therefore, the present invention is to be limited not by the specific disclosure herein, but only by the appended claims.

What is claimed is:

1. A suture anchor comprising:
   a threaded anchor body having a proximal end and a blunt distal end;
   a central bore extending from an opening at the proximal end of the anchor body through a portion of the length thereof;
   four apertures located at a most distal surface of the blunt distal end of the anchor body and in communication with the central bore, wherein the four apertures are arranged in two pairs, each pair of apertures defining the ends of a respective groove extending between the pair of apertures at the distal end of the anchor body, the grooves being parallel and recessed from the most distal surface of the distal end, the grooves defining a ridge extending completely therebetween;
   a first suture passing through a first pair of the four apertures, and through a first one of the grooves; and
   a second suture passing through a second pair of the four apertures, and through a second one of the grooves;
   wherein the first and second suture are separated at the distal end of the anchor body by the ridge.

2. The suture anchor according to claim 1, wherein the apertures are connected to respective passageways that extend through the anchor body substantially parallel to a longitudinal axis of the anchor body.

3. The suture anchor according to claim 1, wherein the centers of the apertures of each pair are spaced apart from each other by about 0.05 to about 0.08 inches.

4. The suture anchor according to claim 1, wherein the central bore has a hexagonal cross-sectional shape.

5. The suture anchor according to claim 1, wherein the central bore has a cross-sectional shape so as to accommodate a driver head for driving the suture anchor.

6. A suture anchor assembly for attachment of tissue to bone, the suture anchor assembly comprising:
   a suture anchor comprising an anchor body having a distal end, a proximal end, a longitudinal axis, an outer surface and a central bore located at the proximal end;
   four suture apertures located at the distal end of the anchor body, wherein the four apertures are arranged in two pairs, each pair of apertures defining the ends of a respective groove extending between the pair of apertures at the distal end of the anchor body, the grooves being parallel and recessed from the most distal surface of the distal end, the grooves defining a ridge extending completely therebetween;
   a first suture strand attached to the suture anchor and passing slidingly through the central bore, through the a first pair of the four apertures, and through a first one of the grooves; and
   a second suture strand passing slidingly through the central bore, through a second pair of the four apertures, and through a second one of the grooves;
   wherein the first and second suture strands are separated at the distal end of the anchor body by the ridge.

7. The suture anchor assembly of claim 6, wherein each of the suture apertures is connected to a respective distal passage comprising a proximal passage end and a distal passage end, the proximal passage end being in communication with the central bore, and the distal passage end being in communication with an aperture located at a most distal surface of the anchor body.

8. The suture anchor assembly of claim 7, wherein the anchor body comprises a plurality of thread flights extending from the outer surface of the anchor body.

9. The suture anchor assembly of claim 6, wherein the length of the suture passages is about one third the length of the body member.

* * * * *

UNITED STATES PATENT AND TRADEMARK OFFICE
CERTIFICATE OF CORRECTION

| | | |
|---|---|---|
| PATENT NO. | : 8,579,940 B2 | Page 1 of 1 |
| APPLICATION NO. | : 11/097180 | |
| DATED | : November 12, 2013 | |
| INVENTOR(S) | : Peter J. Dreyfuss et al. | |

It is certified that error appears in the above-identified patent and that said Letters Patent is hereby corrected as shown below:

On the title page item (75) Inventors, please change the following:

change "William C. Benavits" to --William C. Benavitz--.

Signed and Sealed this

Eleventh Day of February, 2014

Michelle K. Lee
*Deputy Director of the United States Patent and Trademark Office*